(12) United States Patent
Faircloth

(10) Patent No.: US 11,786,746 B2
(45) Date of Patent: Oct. 17, 2023

(54) MAGNETIC HYPERTHERMIA TREATMENT SYSTEMS AND METHODS

(71) Applicant: Brian Faircloth, Evergreen, CO (US)

(72) Inventor: Brian Faircloth, Evergreen, CO (US)

(*) Notice: Subject to any disclaimer, the term of this patent is extended or adjusted under 35 U.S.C. 154(b) by 287 days.

(21) Appl. No.: 17/379,433

(22) Filed: Jul. 19, 2021

(65) Prior Publication Data
US 2022/0016433 A1 Jan. 20, 2022

Related U.S. Application Data

(60) Provisional application No. 63/053,163, filed on Jul. 17, 2020.

(51) Int. Cl.
*A61N 2/00* (2006.01)
*A61N 2/02* (2006.01)
*A61N 1/40* (2006.01)

(52) U.S. Cl.
CPC .............. *A61N 2/004* (2013.01); *A61N 2/02* (2013.01); *A61N 1/403* (2013.01)

(58) Field of Classification Search
None
See application file for complete search history.

(56) References Cited

U.S. PATENT DOCUMENTS

| | | | |
|---|---|---|---|
| 4,574,782 A | 3/1986 | Borrelli et al. | |
| 4,974,595 A | 12/1990 | Nordenstrom | |
| 5,141,487 A | 8/1992 | Liprie | |
| 6,607,478 B2 | 8/2003 | Williams | |
| 8,696,545 B2 | 4/2014 | Nicoson et al. | |
| 2002/0004625 A1 | 1/2002 | Asano | |
| 2002/0058852 A1 | 5/2002 | Halpern et al. | |
| 2005/0090732 A1* | 4/2005 | Ivkov | A61P 25/28 324/318 |
| 2007/0231393 A1* | 10/2007 | Ritter | A61K 9/0009 436/526 |
| 2012/0289955 A1* | 11/2012 | Marc | A61K 8/19 606/41 |
| 2012/0310034 A1 | 12/2012 | Creighton et al. | |
| 2013/0261710 A1 | 10/2013 | Won et al. | |

FOREIGN PATENT DOCUMENTS

| | | |
|---|---|---|
| CN | 107661499 A | 2/2018 |
| WO | 2009/005659 A1 | 1/2009 |
| WO | 2016/010977 A1 | 1/2016 |

OTHER PUBLICATIONS

PCT International Search Report for PCT/US2021/042257, dated Nov. 23, 2021, 2 pages.

* cited by examiner

*Primary Examiner* — Carrie R Dorna
(74) *Attorney, Agent, or Firm* — Acuity IP, LLC; Nathan S. Cassell

(57) ABSTRACT

Exemplary magnetic hyperthermia treatment systems and methods involve placing a conducting particle having a diameter of 500 microns within a tumor of a patient; and heating the conducting particle with an oscillating magnetic field. In some cases, the particle has a diameter or dimension with a value within a range of about 20 microns to about 1000 microns. In some cases, particle has a diameter or dimension with a value that is greater than 1000 microns.

18 Claims, 20 Drawing Sheets

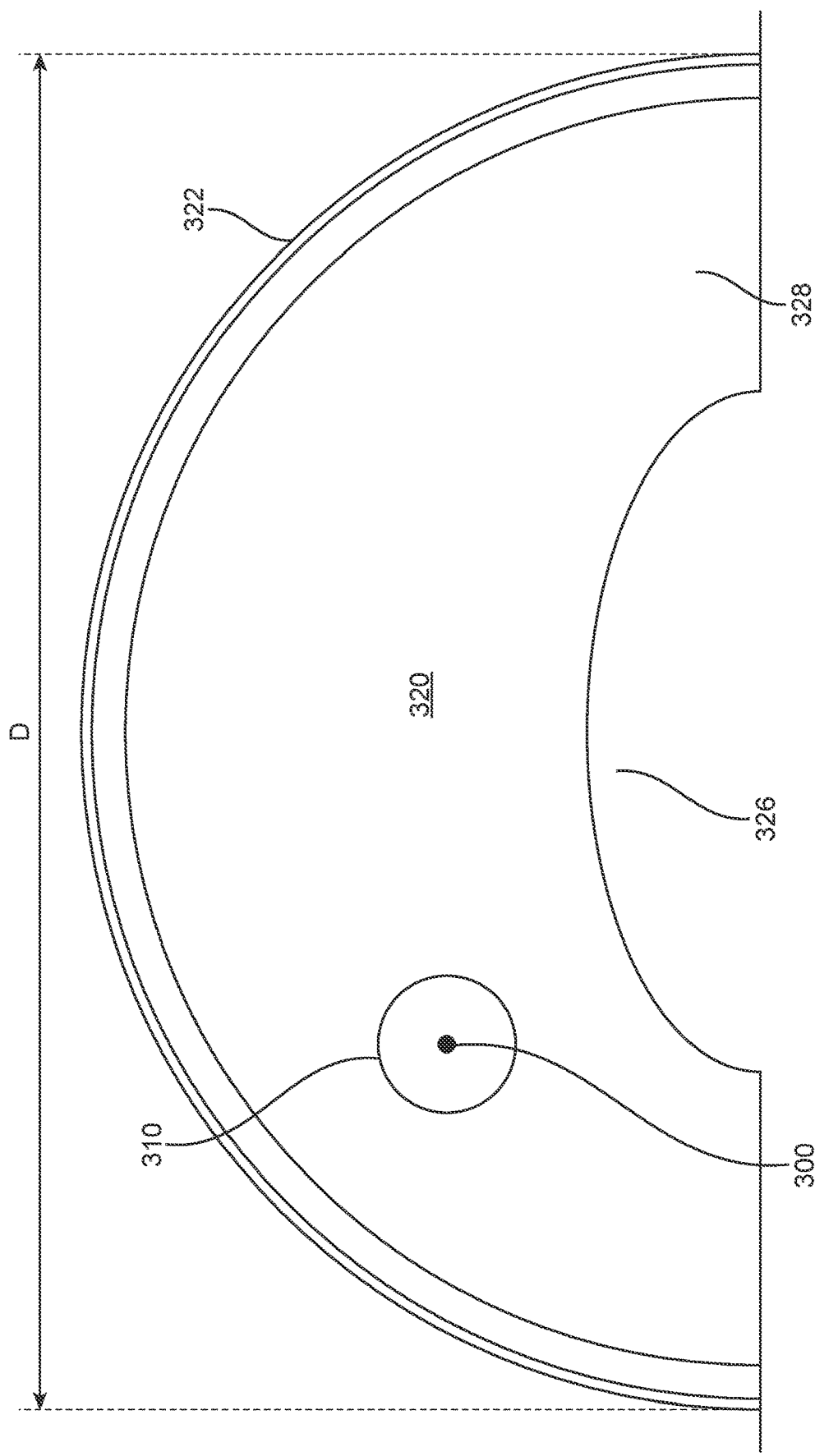

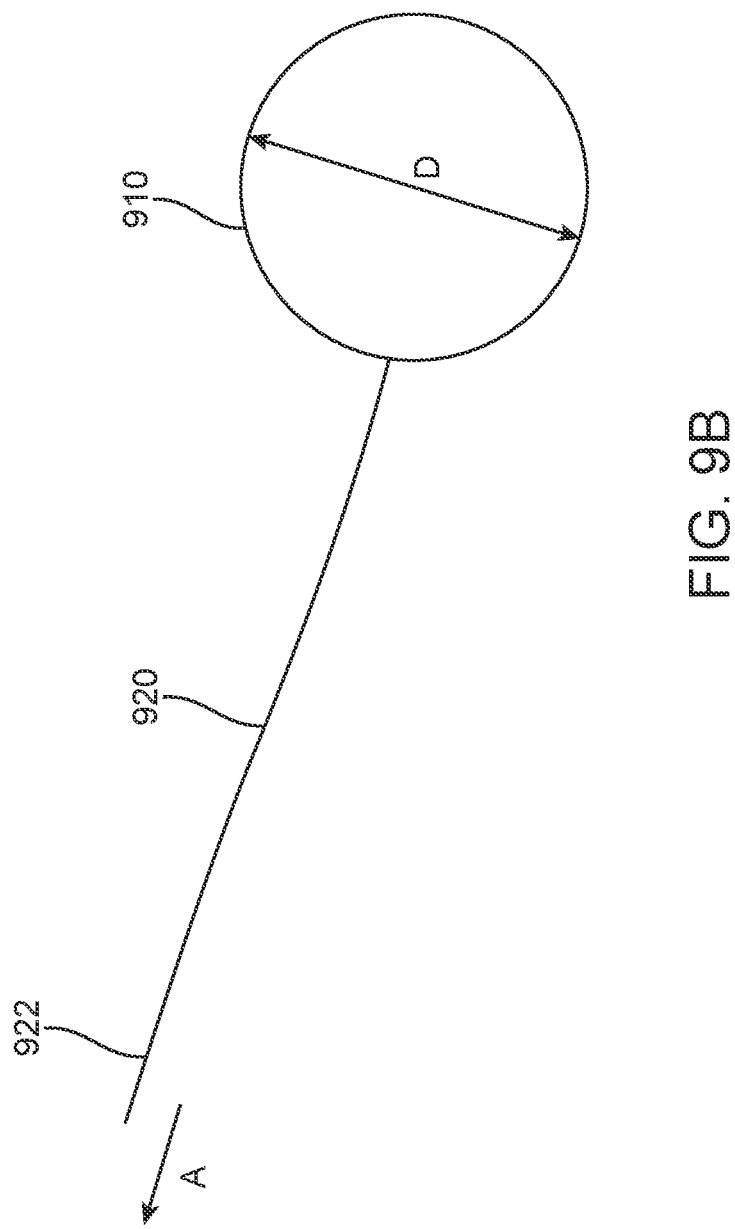

MAGNETIC HYPERTHERMIA TREATMENT SYSTEMS AND METHODS

CROSS-REFERENCE

This application claims the benefit of U.S. Provisional Patent Application No. 63/053,163 filed Jul. 17, 2020, the content of which is incorporated herein by reference.

BACKGROUND

Embodiments of the present invention related generally to systems and methods for treating cancer, and in particular, to treatment systems and methods for delivering hyperthermia treatments to a cancerous tumor.

Various treatment devices and methods have been proposed for treating cancerous tumors. Often, such techniques require making incisions in the body of a patient, delivering ionizing radiation, or administering drugs.

Although these treatment modalities can provide relief to patients presenting with cancer tumors, still further improvements are desired. Embodiments of the present invention address at least some of these outstanding needs.

SUMMARY

Embodiments of the present invention encompass systems and methods for delivering hyperthermia treatments to a cancerous tumor. Exemplary embodiments encompass the minimally invasive treatment of cancerous tumors that does not require an incision, harmful ionizing radiation, or drugs. Systems and methods disclosed herein enable the treatment of some cancers that are resistant to other treatments or considered difficult or impossible to treat otherwise. While primarily discussed herein with reference to the treatment of cancer, it is understood that the disclosed treatment modalities should not be limited to the treatment of cancer. For example, embodiments of the present invention encompass the treatment of any condition that can benefit from the application of intense heat to a localized area inside the body.

In a first aspect, embodiments of the present invention encompass systems and methods for treating a patient presenting with a cancerous tumor. Exemplary methods can include placing a conducting particle within the tumor of the patient, where the conducting particle has a diameter with a value within a range from about 20 microns to about 1000 microns, and heating the conducting particle with an oscillating magnetic field. In some cases, the value of the diameter is about 500 microns. In some cases, the step of placing the conducting particle within the tumor of the patient involves delivering the conducting particle with a delivery device such as a biopsy needle, a bone marrow syringe, or a standard syringe. In some cases, the conducting particle is attached with a filament. In some cases, the filament includes a low conductivity material. In some cases, the particle is attached with the filament via an epoxy coupling, a welded coupling, or a clamped coupling. On some cases, the oscillating magnetic field is produced by a magnetic field generation device that is in operative association with a control unit. In some cases, the conducting particle includes a chemically inert material. In some cases, the conducting particle includes a material such as gold or titanium. In some cases, the conducting particle includes a material such as a ferromagnetic material or a ferrimagnetic material.

In another aspect, embodiments of the present invention encompass systems for treating a patient presenting with a cancerous tumor. Exemplary systems can include a conducting particle configured to be placed within the tumor of the patient, where the conducting particle has a diameter with a value within a range from about 20 microns to about 5000 microns. Systems can also include a magnetic field generation device, and a computer system in operative association with the magnetic field generation device. The computer system can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the magnetic field generation device to generate an oscillating magnetic field that heats the conducting particle. According to some embodiments, a frequency of the oscillating magnetic field has a value within a range from about 10 kHz to about 10000 kHz. In some embodiments, a frequency of the oscillating magnetic field has a value of about 50 kHz. In some embodiments, an oscillating magnetic field produced at the site of the tumor can have a field strength with a value within a range from about 1 milliTesla to about 10 Tesla. In some cases, a strength of the oscillating magnetic field has a value of about 0.1 Tesla.

In still another aspect, embodiments of the present invention encompass systems and methods of providing heat to a treatment location of a patient. Exemplary methods can include placing a conducting particle at the treatment location of the patient, where the conducting particle has a dimension with a value within a range from about 20 microns to about 5000 microns. Methods can also include heating the conducting particle with an oscillating magnetic field, such that the heated conducting particle provides heat to the treatment location. In some embodiments, the conducting particle has a shape such as a sphere, a rectangular volume, an ellipsoid, a rod, or a cylinder. In some embodiments, the dimension has a value of about 500 microns. In some embodiments, the treatment location of the patient is within a tumor. In some embodiments, the tumor is a cancer tumor. In some embodiments, the conducting particle is attached with a filament, and the method further includes withdrawing the conducting particle from the treatment location after the conducting particle provides heat to the treatment location, by pulling on the filament.

BRIEF DESCRIPTION OF THE DRAWINGS

The novel features of the invention are set forth with particularity in the appended claims. A better understanding of the features and advantages of the provided system and methods will be obtained by reference to the following detailed description that sets forth illustrative embodiments, in which the principles of the invention are utilized, and the accompanying drawings of which:

FIG. 3 depicts aspects of exemplary magnetic hyperthermia treatment systems and methods, according to embodiments of the present invention.

FIGS. 9A to 9D depict aspects of exemplary magnetic hyperthermia treatment systems and methods, according to embodiments of the present invention.

DETAILED DESCRIPTION

Figure 1:
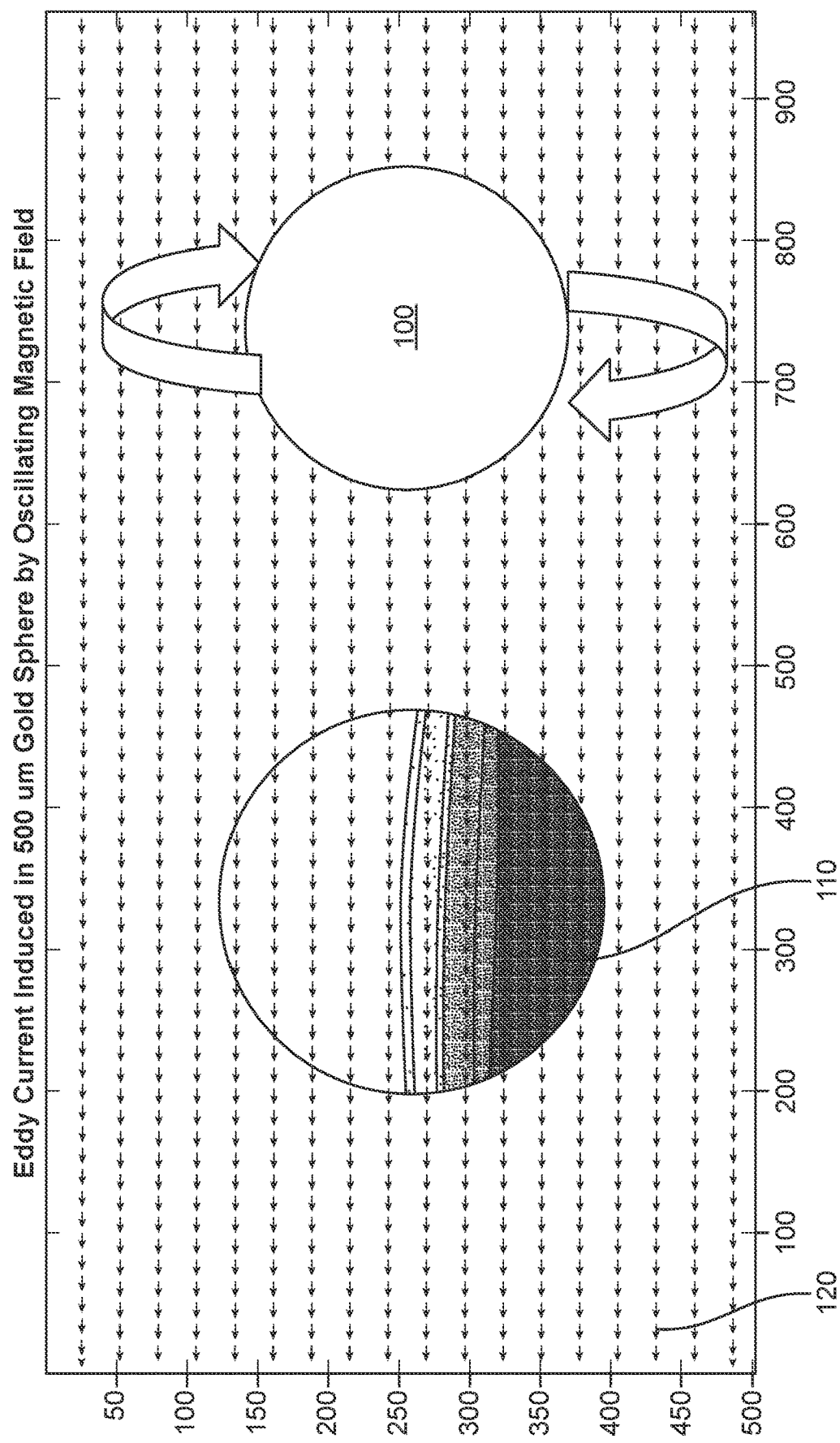
FIG. 1 illustrates aspects of eddy currents induced in a particle by an oscillating magnetic field, according to embodiments of the present invention.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

According to Faraday's law, a changing magnetic field will produce an electric field (i.e. an electromotive force (EMF)) in space. According to Ohm's law, $J=\sigma E$, a current will be induced in the conductor by the electric field. Where J is the current density, $\sigma$ is the conductivity of the material, and E is the electric field. These currents are known as eddy currents because they typically move in circular vortex patterns resembling eddies in fluids. This is a non-contact method. Eddy currents can be induced in conductors from a remote distance. When current flows in a conducting material, power will be dissipated in the conductor (i.e. resistive heating) according to the formula: PowerDissipated=$I^2$ R, wherein I is the current and R is the resistance of the material.

The total process is known as inductive heating. When metals are ferromagnetic (steel or similar) a secondary process known as magnetic hysteresis losses for additional heating of the metal can occur.

Induction heating can be used to heat an electrically conducting object with electromagnetic induction, and heat is generated in the object by eddy currents. In some cases, an electromagnet and an electronic oscillator can be used to pass a high-frequency alternating current through the electromagnet, and in turn, the alternating magnetic field penetrates the object and generates electric eddy currents therein, thereby heating the object.

In exemplary embodiments, the object can include a conducting material, such as metal. Exemplary metals include gold or titanium. In some embodiments, the object can include a ferromagnetic or ferrimagnetic material. In some cases, the object can include iron. When the object includes a magnetic material, heat can be generated by magnetic hysteresis losses.

In hyperthermia treatments, body tissue is exposed to very high temperatures in order to treat cancer and other medical conditions. In some cases, localized hyperthermia is used to heat a very small area, which may be in or at a cancer tumor. Exemplary treatments can involve heating the tumor with induction heating and/or magnetic hysteresis, so as to destroy it, without negatively impacting the surrounding tissue or with minimal negative impact to the surrounding tissue.

According to some embodiments of the present invention, one or more particles are placed inside of a tumor of a patient, and the patient is positioned in an alternating magnetic field. The application of the field causes the temperature of the particle(s) to increase, thereby heating the tumor and destroying it, or otherwise compromising the viability of the tumor.

Body tissue is highly transparent to magnetic fields. Body tissues typically have magnetic permeabilities very close to 1 in static to radio frequency regimes. Thus, a magnetic field will pass through the human body practically unperturbed.

Exemplary hyperthermia treatments disclosed herein do not require the application of electric fields to the body. Body tissue can have significant differences or non-uniformities in electric permittivity and conductivity which can distort or significantly diminish the electric field as it passes through the body.

Exemplary hyperthermia treatments disclosed herein do not require the application of photothermal therapy or photodynamic therapy which use light, usually infrared, to treat tumors by heating the tissue. Photodynamic therapy injects a photosensitive substance into the tumor to absorb the light and provide differentiation of the tumor from the surrounding tissue. Human tissue typically has large scatter and absorption coefficients. Thus, these therapies can only treat tumors close the surface and/or are limited in their ability to be localized.

Exemplary hyperthermia treatments disclosed herein do not require the application of microwaves to the body of a patient. Microwaves can suffer from lack of differentiation from the tumor and surrounding tissue, especially tissue co-located between the application point and the tumor.

Turning now to the drawings, FIG. 1 depicts aspect of eddy currents 110 induced in a 500 micron (diameter) gold sphere or particle 100 by an oscillating magnetic field 120. According to Lenz's law the eddy currents will flow such that the magnetic field produced by the eddy current will resist changes in the external magnetic field. A metallic sphere in a uniform oscillating magnetic field (as shown here) will produce an eddy current that flows azimuthally around the outside radius of the sphere. In the analyses that follow a sphere is used as the base shape, but other shapes will have different current characteristics and may have different efficiencies at generating heat. Exemplary shapes include cubes, rectangular volumes, ellipsoids, rods, cylinders, and the like. Further, a uniform magnetic field is used as an example, although embodiments of the present invention encompass the use of more complicated magnetic fields which may have different efficiencies.

According to some system and method embodiments of the present invention, a particle can have a diameter or dimension (e.g. height, width, or length) with a value within a range from about 20 microns to about 1000 microns. In some cases, a particle can have a diameter or dimension with a value of about 500 microns. In some cases, a particle can have a diameter or dimension with a value that is greater than 1000 microns. In some cases, a particle can have a diameter or dimension (e.g. height, width, or length) with a value within a range from about 20 microns to about 5000 microns. In some cases, a particle can have a diameter or dimension (e.g. height, width, or length) with a value within a range from about 10 microns to about 5000 microns.

Conducting spheres can be inserted into the body, for example within or at a tumor. Depending on the size of the sphere to be used, a sphere or spheres can be inserted into the tumor using a syringe or a modified biopsy needle (e.g. which has been modified to deliver material rather than extract it). In some cases, the delivery device can be a standard syringe. In some cases, the delivery device can be a bone marrow syringe. Any of a variety of methods can be used to insert microscopic (or mesoscopic) conducting particles into the tumor in a minimally invasive way, or otherwise at or in contact with the tumor, and this can be done even when the tumor may be behind bone.

Figure 2A:
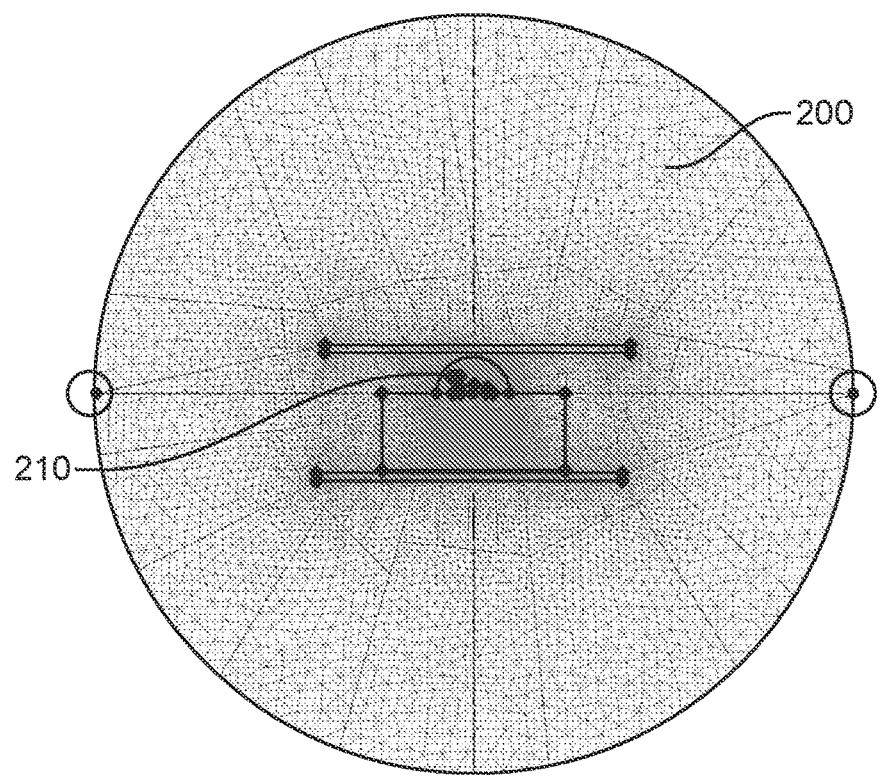
FIGS. 2A and 2B depict aspects of exemplary magnetic hyperthermia treatment systems and methods, according to embodiments of the present invention.
Figure 2B:
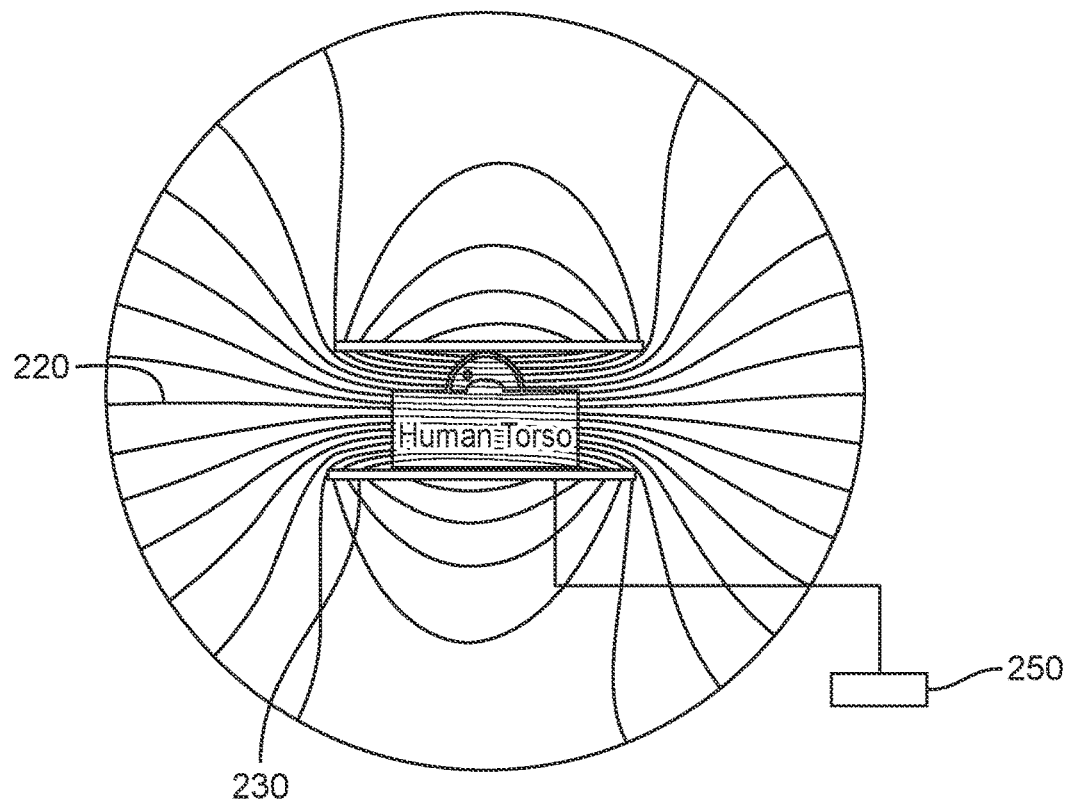

FIGS. 2A and 2B depict aspects of exemplary magnetic hyperthermia treatment systems and methods. A finite element simulation (FEM) 200 of a single 500 micron gold particle 210 inserted into a breast tumor is illustrated in FIG. 2A. As shown in FIG. 2B, magnetic fields 220 penetrate the human body practically unperturbed. This represents a major advantage over electric fields, microwaves, infrared, visible light, and UV light. And unlike X-ray or proton beams or electron beams, magnetic fields are non-ionizing (i.e. cause little to no damage to DNA/RNA). In an exemplary simulation, a high current coil 230 is used to produce the magnetic field. The coil is 40 cm long and 24 cm in diameter with 40 wraps and 1000 amps of current. This produces a 0.1 Tesla field at the site of the tumor. As can be seen the field is relatively uniform in the area of interest. According to some embodiments, a coil can be a component of a magnetic field generation device. As shown here, a coil 230 or magnetic field generation device can be in operative association with a processor or control unit 250. The human body or patient illustrated in FIG. 2B includes a breast with a tumor, aspects of which are depicted in other drawings throughout the application (e.g. FIG. 3). According to some embodiments, a magnetic field produced at the site of the tumor can have a field strength with a value within a range from about 1 milliTesla to about 10 Tesla.

FIG. 3 depicts aspects of a breast tumor treatment model. This model is based on commonly recognized magnetic, electrical, and thermal properties of the inserted gold particle and the relevant human tissues. For example, as shown here, the particle 300 can be a gold sphere having a diameter of about 500 microns. The tumor 310 can have a diameter of about 1.0 cm. The breast 320 can have a diameter D of about 10 cm. The breast 320 can include a skin layer 322, a fat layer 324, muscle 326, and gland 328.

Figure 4A:
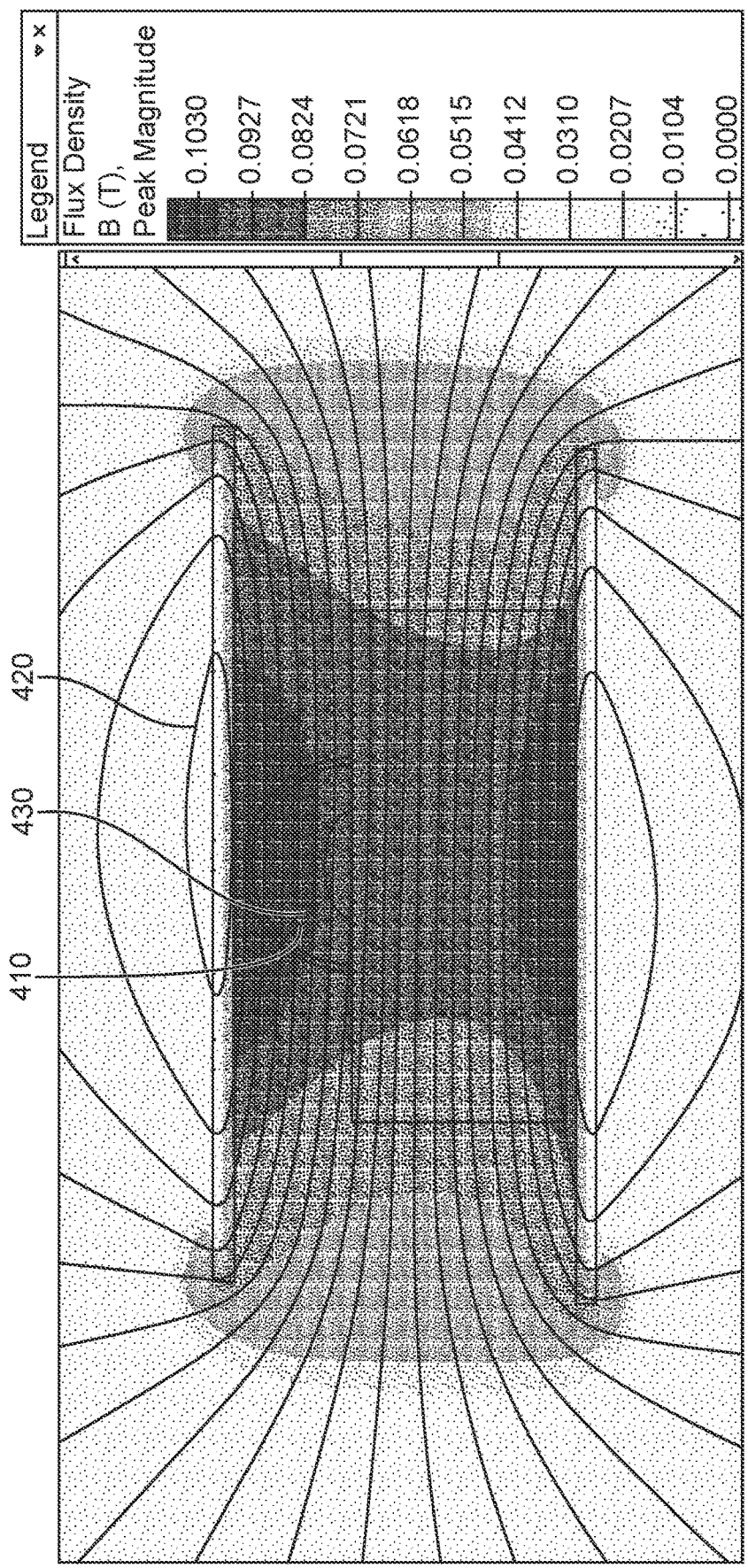
FIGS. 4A and 4B depict aspects of exemplary magnetic hyperthermia treatment systems and methods, according to embodiments of the present invention.
Figure 4B:
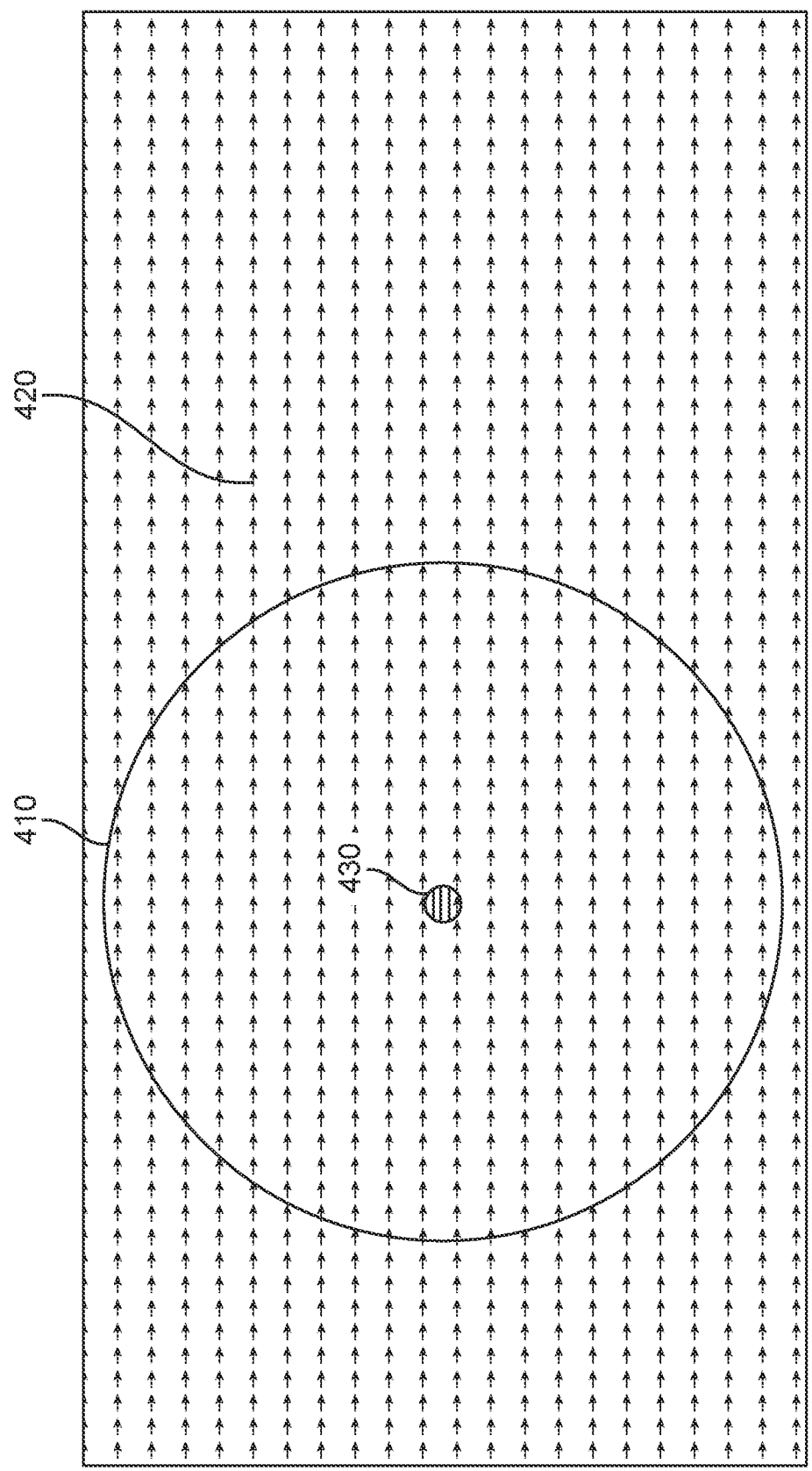

FIGS. 4A and 4B depict aspects magnetic field models according to embodiments of the present invention. At the site of the tumor 410, the magnetic field strength is 0.1 Tesla sinusoidally oscillating at a frequency of 50 kHz. The oscillation of the magnetic field 420 heats the gold particle 430 by producing eddy currents within the gold sphere 430. In some embodiments, a frequency can have a value within a range from 10 kHz to 10000 kHz. According to some embodiments, a magnetic field produced at the site of the tumor can have a field strength with a value within a range from about 1 milliTesla to about 10 Tesla.

Figure 5A:
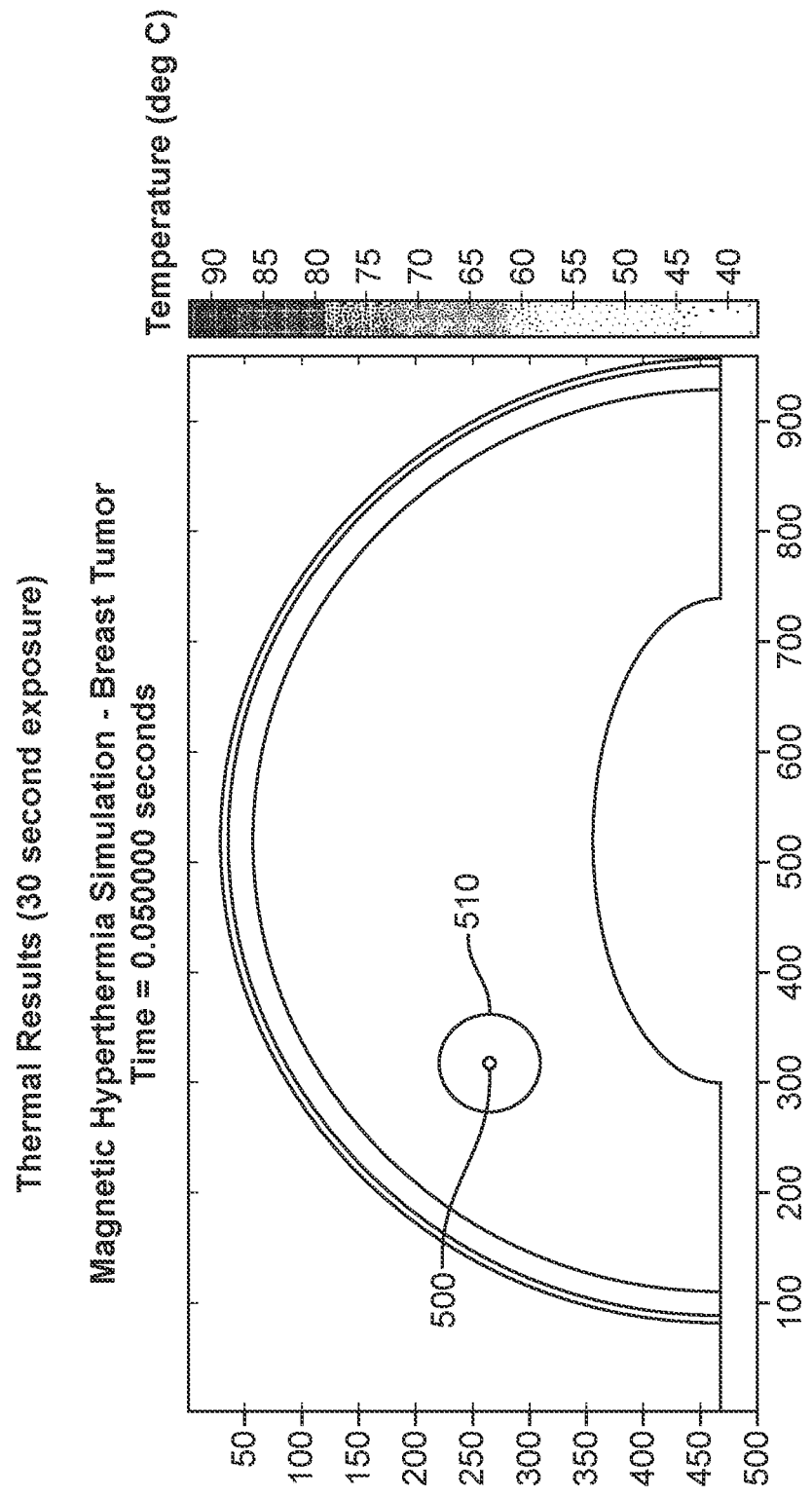
FIGS. 5A, 5B, and 5C depict aspects of exemplary magnetic hyperthermia treatment systems and methods, according to embodiments of the present invention.
Figure 5B:
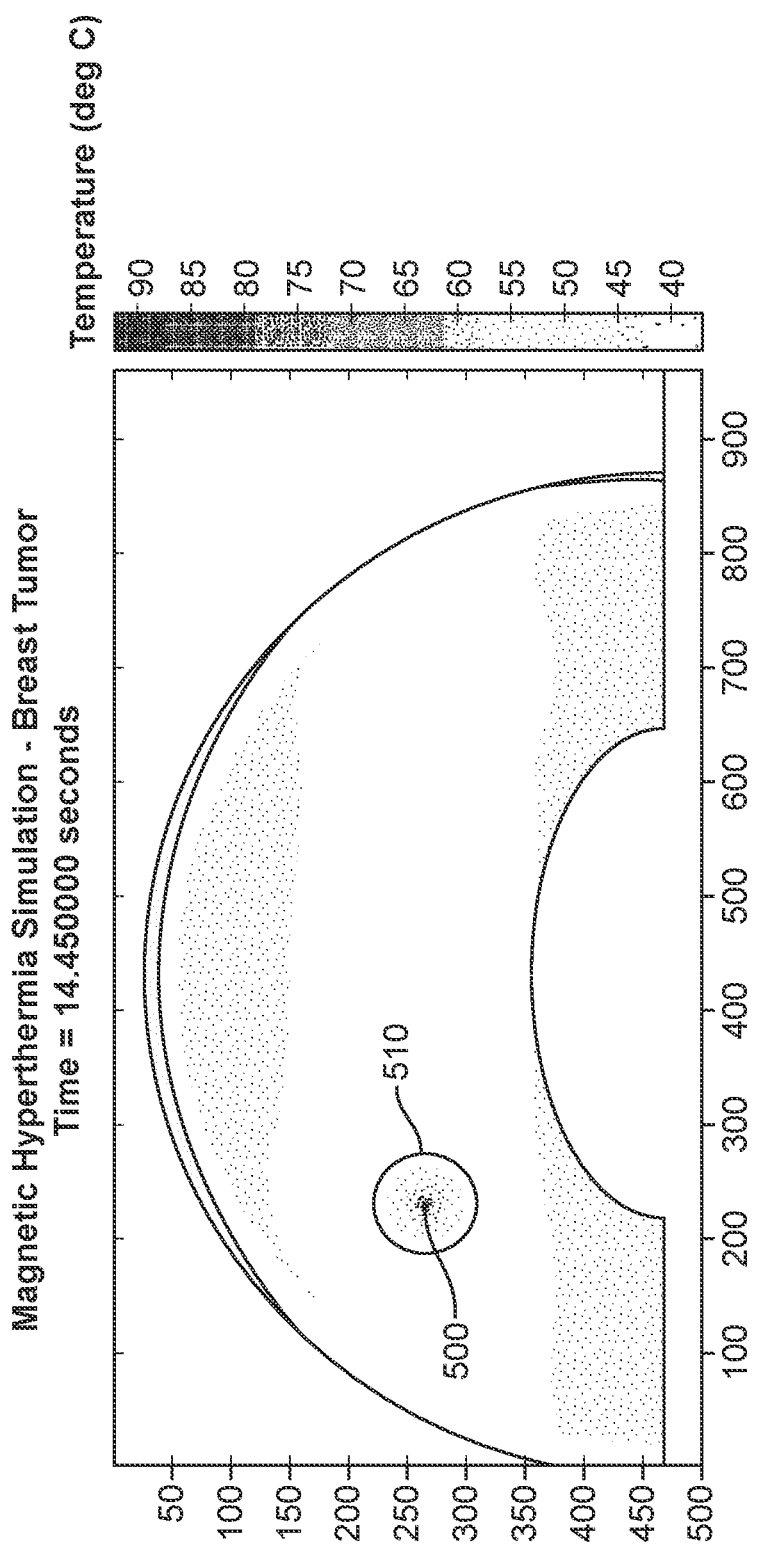
Figure 5C:
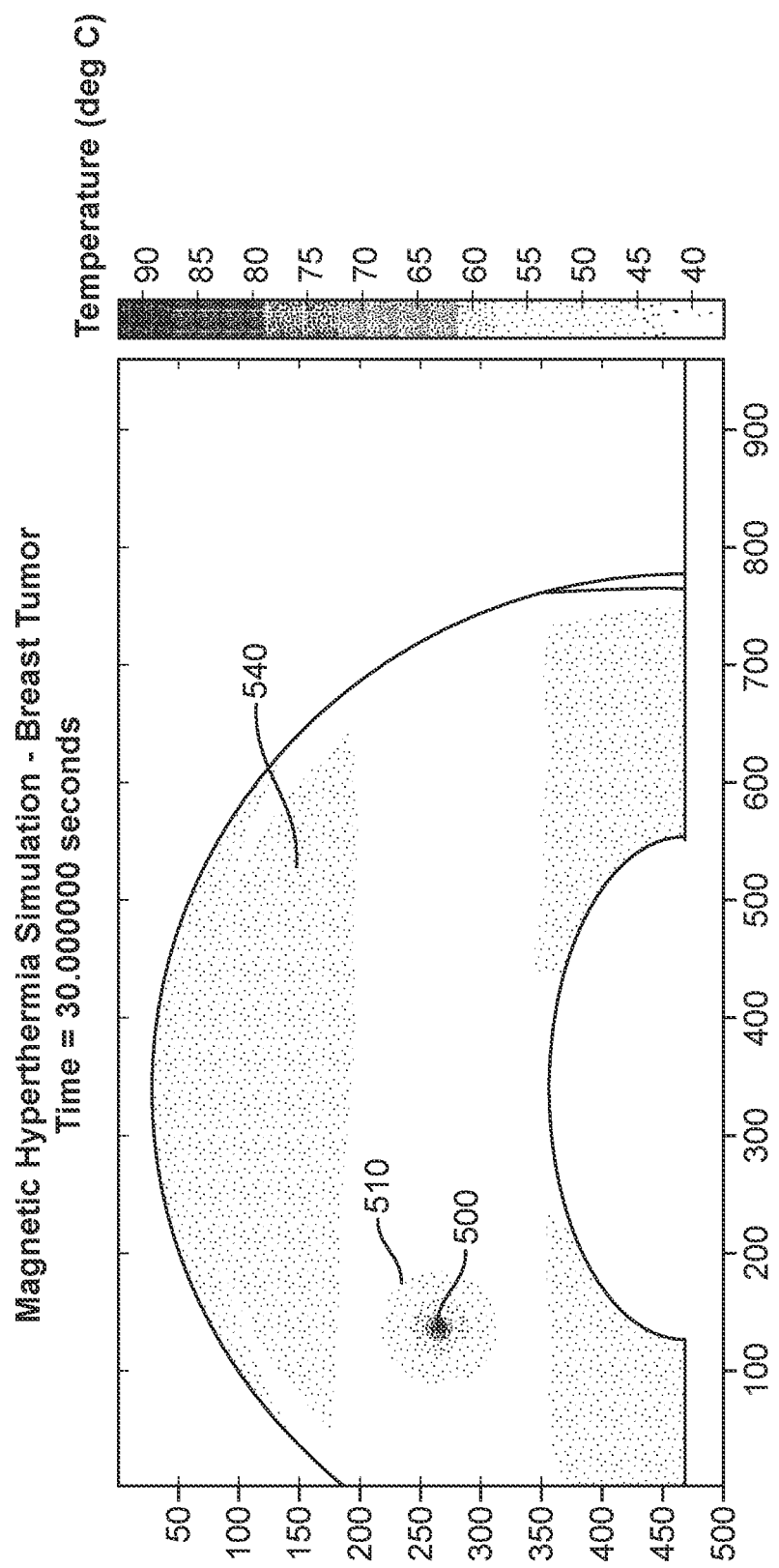
Figure 6:
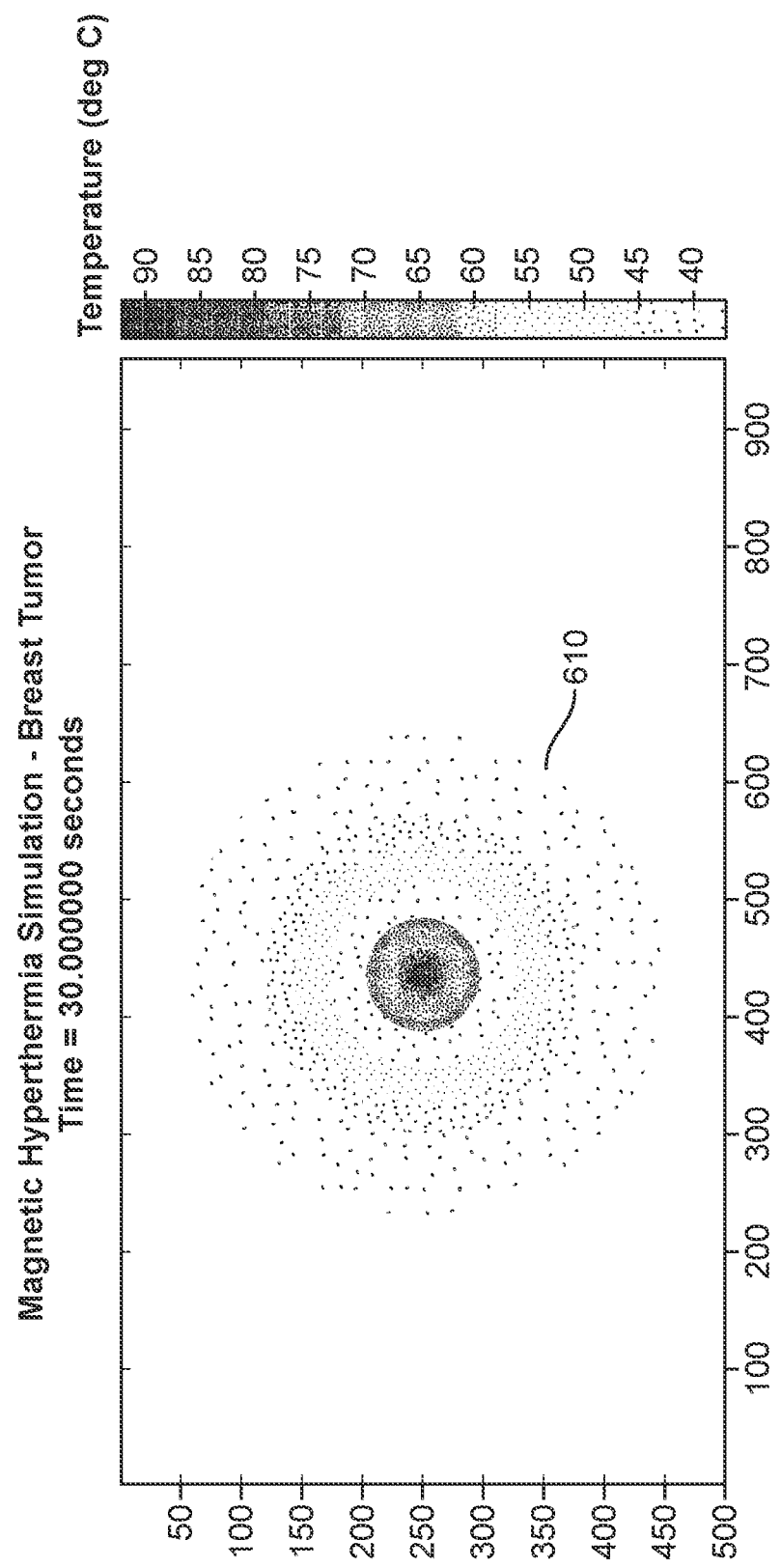
FIG. 6 depicts aspects of exemplary magnetic hyperthermia treatment systems and methods, according to embodiments of the present invention.

FIGS. 5A, 5B, and 5C depict aspects of a magnetic hyperthermia treatment simulation, according to embodiments of the present invention. As shown here, there is little heating of the particle 500 or tumor 510 following 0.05 seconds of exposure to a magnetic field (FIG. 5A). The particle 500 and tumor 510 exhibit some heating following 14.45 second of exposure (FIG. 5B), and further heating following 30 second of exposure (FIG. 5C). FIG. 6 depicts an up-close view of the tumor 610 (corresponding to the image depicted in FIG. 5C). As shown here, with a 30 second exposure the localized area gets to over 90 deg Celsius. By adjusting the current (i.e. magnetic field strength) or frequency or exposure time the temperature can be made to reach several hundred degrees Celsius if desired. It can be seen in these simulations the breast tissue (e.g. at location 540 shown in FIG. 5C) does begin to warm somewhat due its own inductive heating in the magnetic field. This heating, which in some cases may be undesirable, can be mitigated by doing the process in a cool water bath. In the shown simulations, the only cooling mechanism is the convective cooling of the skin itself. A cold water bath would have negligible effect on the localized heating of the gold particle and tumor.

Figure 7A:
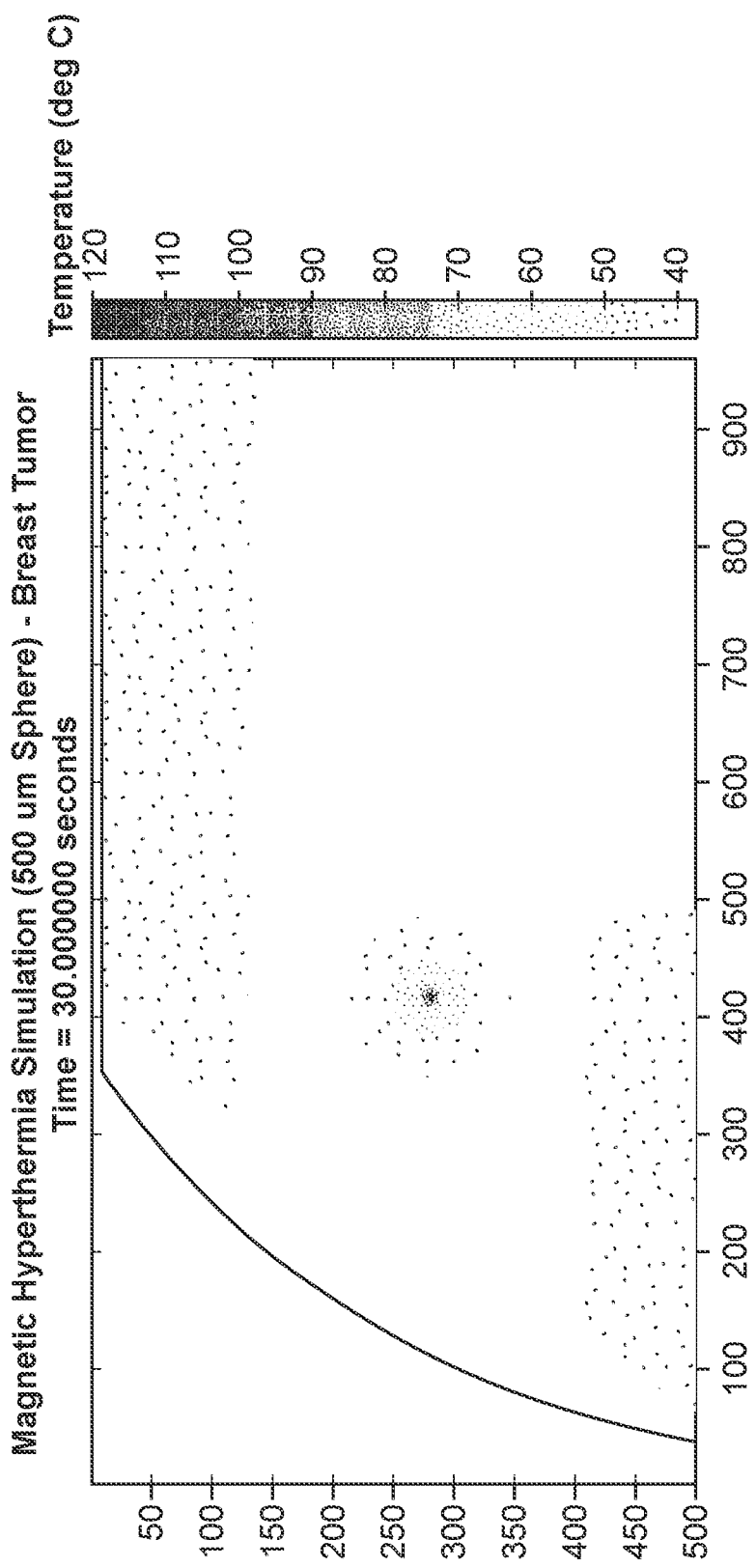
FIGS. 7A and 7B depict aspects of exemplary magnetic hyperthermia treatment systems and methods, according to embodiments of the present invention.
Figure 7B:
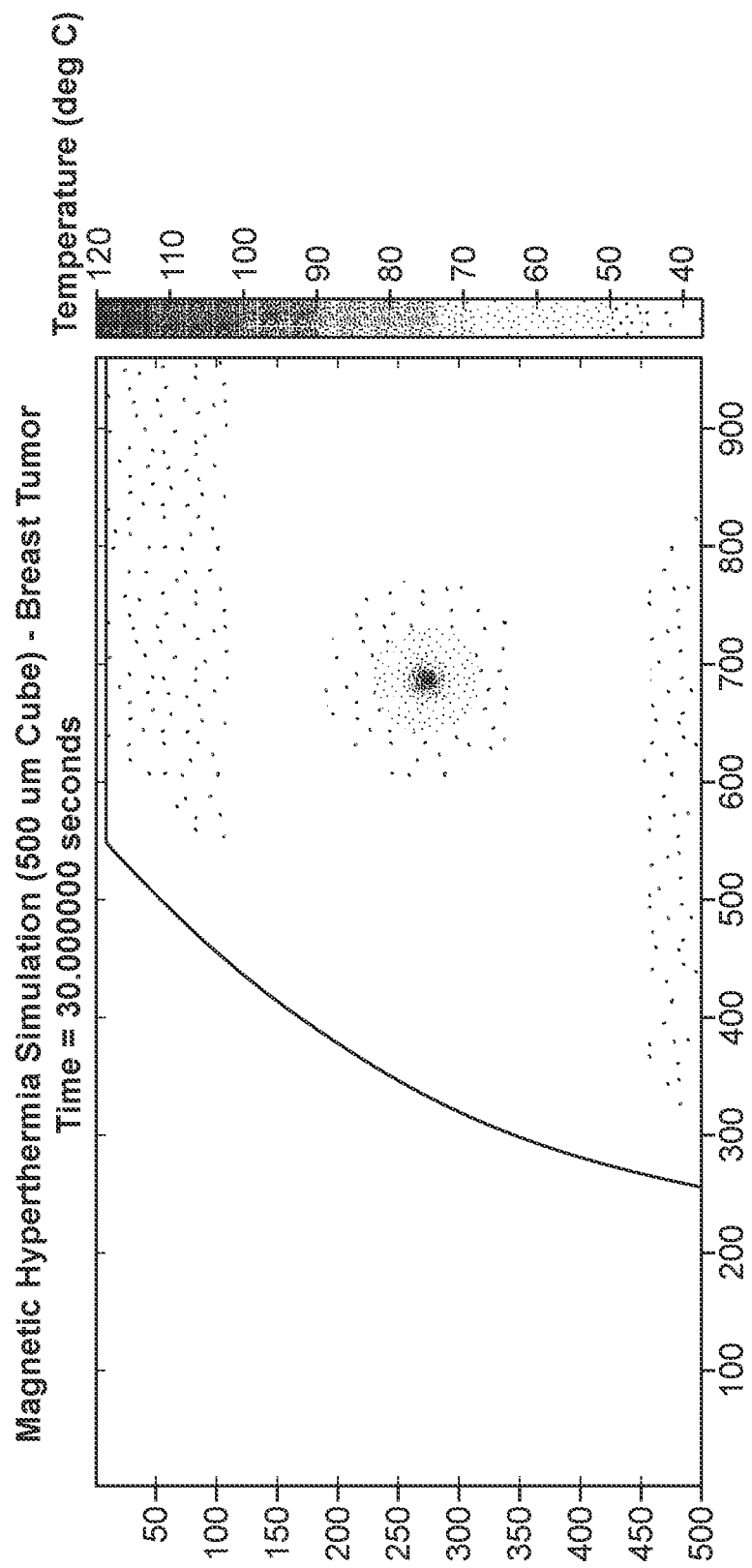
Figure 8A:
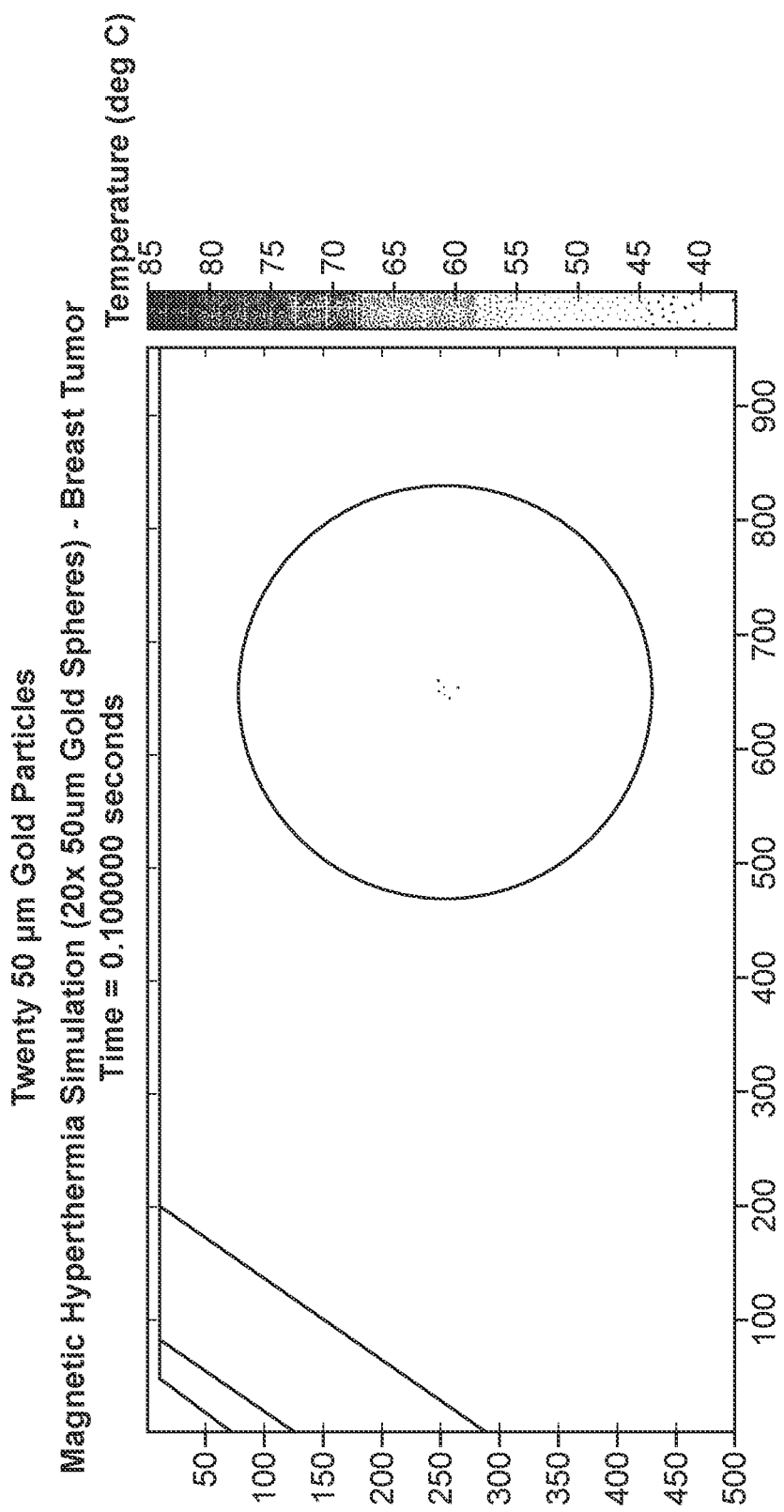
FIGS. 8A to 8D depict aspects of exemplary magnetic hyperthermia treatment systems and methods, according to embodiments of the present invention.
Figure 8B:
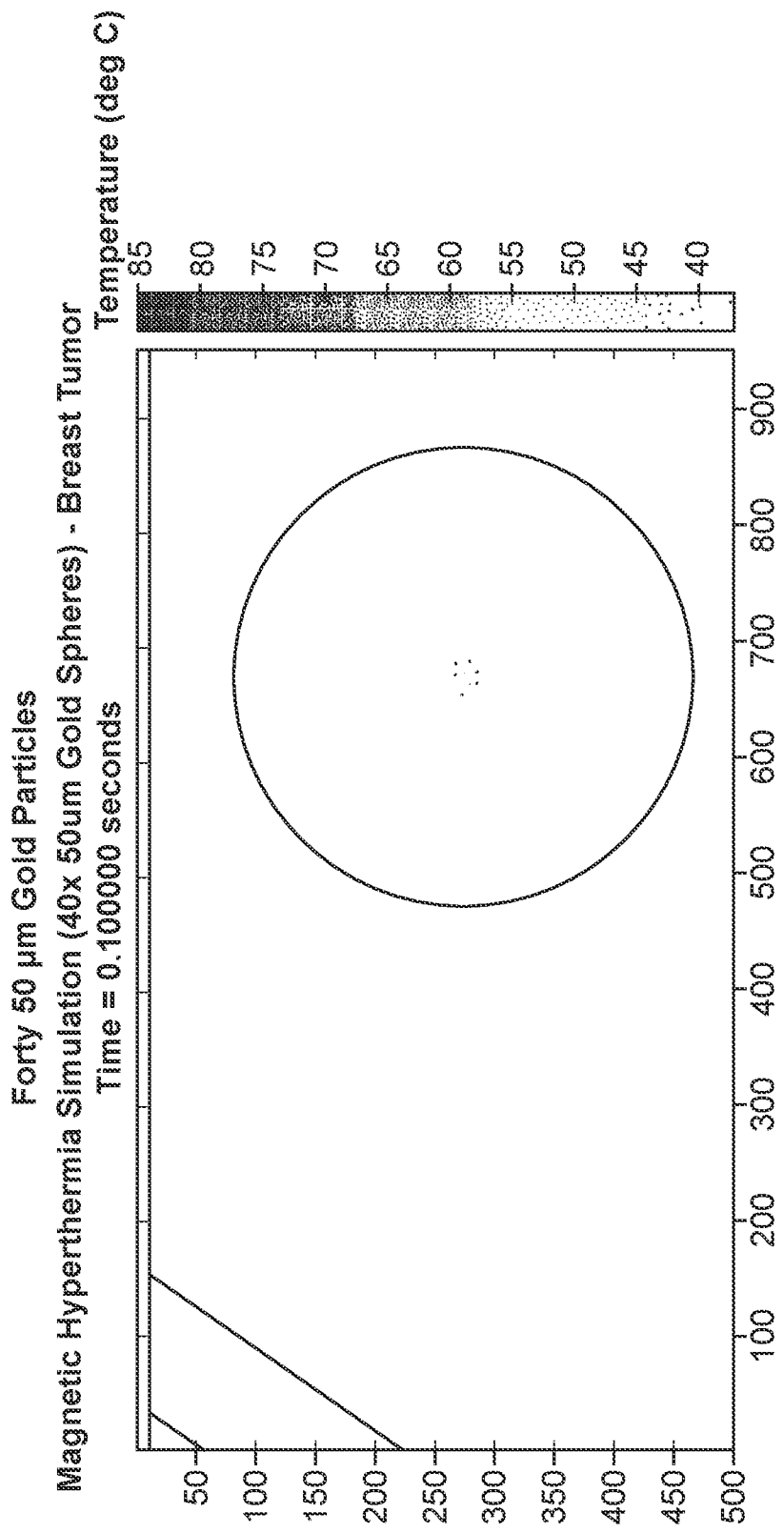
Figure 8C:
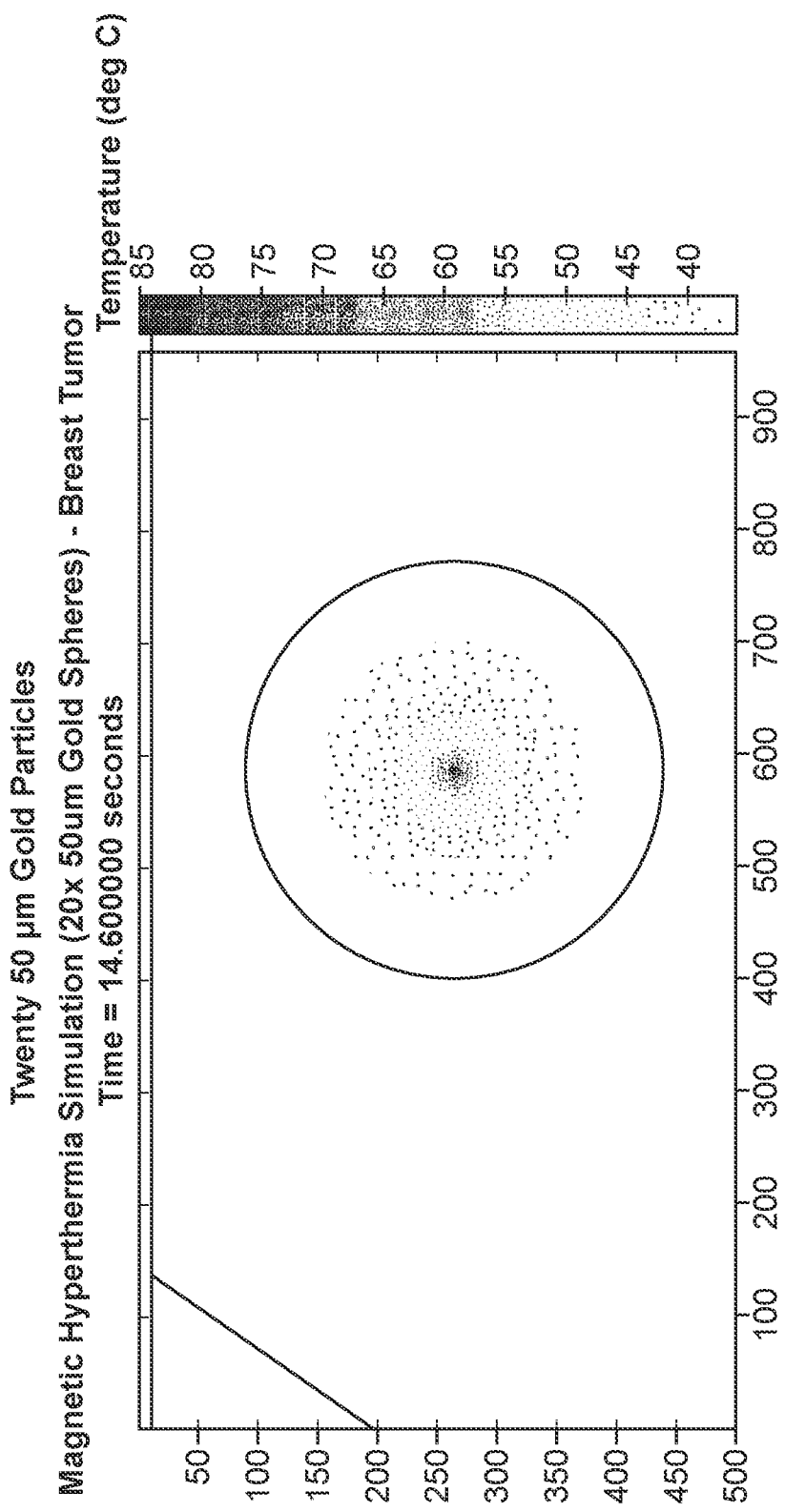
Figure 8D:
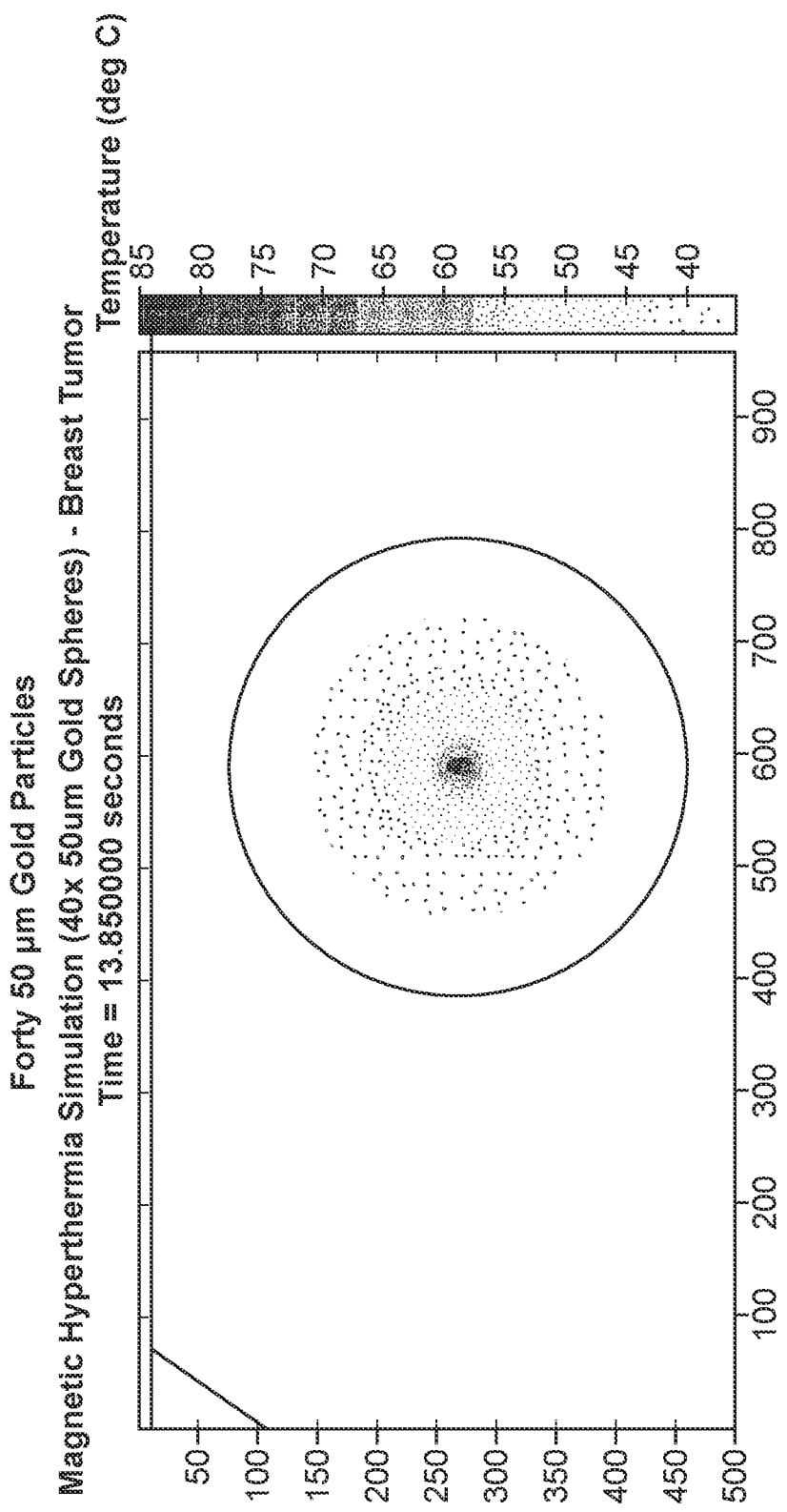

FIGS. 7A and 7B, depict modeled thermal results (30 Second Exposure) for a 500 μm sphere (FIG. 7A) compared to a 500 μm cube (FIG. 7B). The sphere reaches 92 degrees C., while the cube reaches 120 degrees C. with the same 0.1 Tesla, 50 kHz field and a thirty second exposure time. According to some embodiments, a magnetic field produced at the site of the tumor can have a field strength with a value within a range from about 1 milliTesla to about 10 Tesla.

FIGS. 8A to 8D depict aspects of multi-particle simulations. For example, FIGS. 8A and 8C correspond to twenty 50 μm gold particles at 0.10 second and 14.60 seconds, respectively. Likewise, FIGS. 8B and 8D correspond to forty 50 μm gold particles at 0.10 seconds and 13.85 seconds, respectively. In some cases, a larger number of smaller particles may be easier to inject (e.g. using smaller needles). It can be seen that simulation results are similar to the single larger sphere simulation.

Figure 9A:
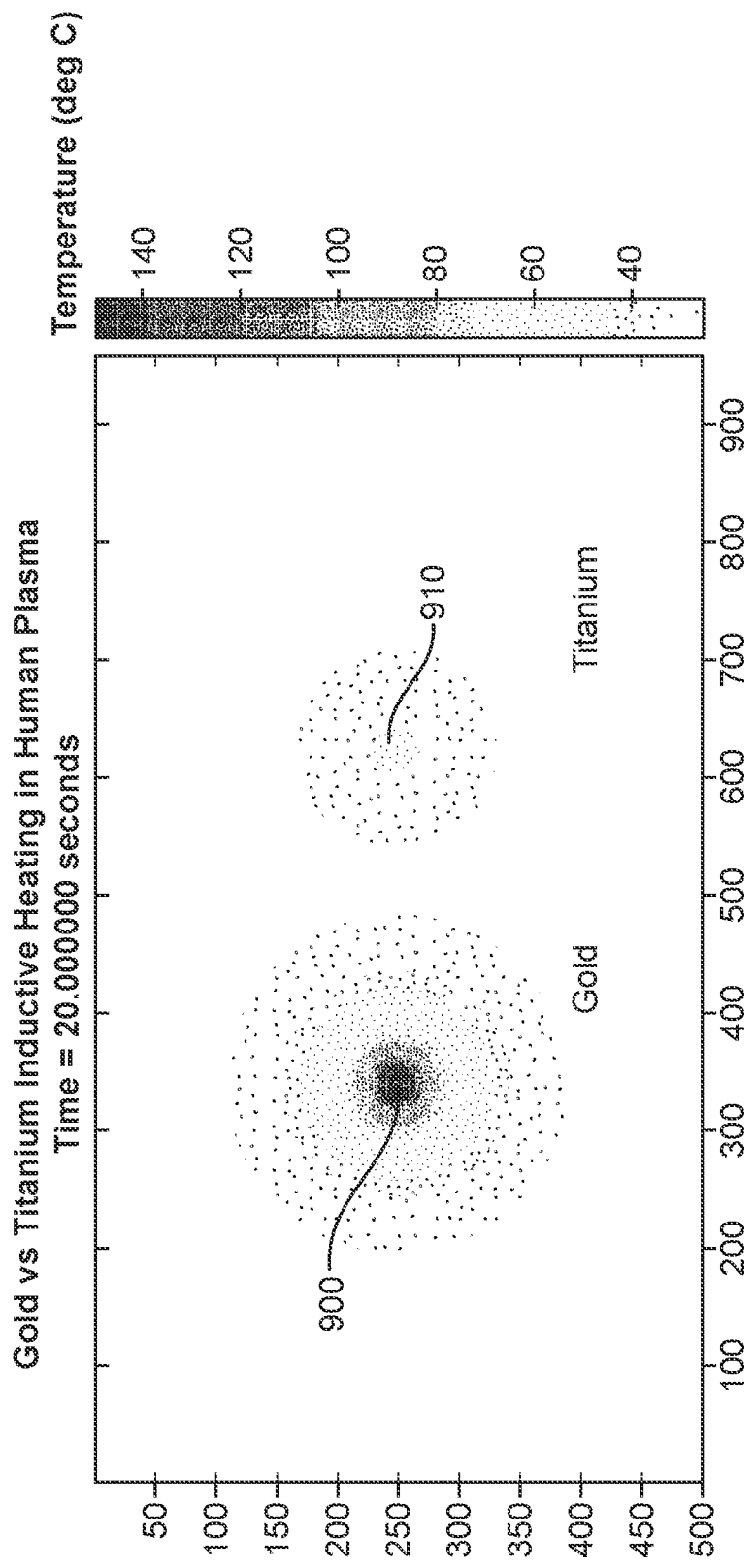

FIG. 9A depicts a modeled comparison of results between 500 micron gold sphere 900 and a 500 micron titanium sphere 910. Embodiments of the present invention encompass the use of any type of conducting material. In exemplary embodiments, the conducting material is gold.

In some cases, the higher the conductivity the more efficient the heating→lower magnetic fields and/or oscillation frequencies which equates to a simpler, smaller machine.

Many metals in high doses in the bloodstream can have deleterious effects or can be toxic. For instance, silver is highly conductive and is non-toxic in the human blood stream. However, in high doses, silver can cause argyria, a condition in which the skin irreversibly turns a bluish-gray color. Gold is chemically inert and has no known negative side effects inside the human body.

Particles can be passivated with polymer coatings or gold plating, however, there may be a finite risk of leeching of the base material into the bloodstream.

Surgical titanium can safely be left in the body. Titanium has a conductivity of $2.38 \times 10^6$ S/m and gold has a conductivity of $4.11 \times 10^7$ S/m. Stainless steel has a conductivity less than titanium.

With regard to hysteresis heating, magnetic materials have a magnetic 'memory' in which they stay magnetized after the magnetic field is removed. When the magnetic field is cycled it requires energy to undo the memorized magnetic field from earlier in the cycle, this energy is converted to heat—hysteresis loss. Magnetic materials have both inductive heating from the eddy currents and the hysteresis losses.

Many known ferromagnetic materials are toxic in high levels in the human blood stream. Stainless steel is a magnetic material. It is possible for nickel and chromium from the steel to leech into the blood stream.

By using microscopic particles (e.g. 500 microns in diameter) it is possible to realize advantages that may be difficult or impossible to achieve when using smaller particles such as particles of nanometer scale. For example, it is easier to induce current in 500 micron particles as compared with smaller particles, such as those on the nanometer scale.

Moreover, when using particles having a 500 micron diameter (or similarly sized particles) it is possible to attach a filament to a particle. In this way, the magnetic hyperthermia particle(s) can be easily removed from the patient following administration of the treatment. For example, FIG. 9B depicts a particle 910 attached with a filament 920. In some cases, the particle 910 can have a diameter of one hundred microns or more, and a high strength, low conductivity filament 920 can be attached to the particle (e.g. with a small hole in the center like a bead, with epoxy, welded, or clamped). In this way the particle 910 can be removed after the procedure is complete, simply by pulling it out of the insertion pathway (e.g. by pulling on a proximal end 922 of the filament 910 in a direction as indicated by arrow A). As shown here, particle 910 has a diameter or dimension D. This would allow for the insertion of any kind of material desired, such as a ferromagnetic materials or more exotic magnetic alloys, because there would be no concern about long term toxicity of the material in the body. In this way both hysteresis heating and eddy current heating could be utilized.

Figure 9C:
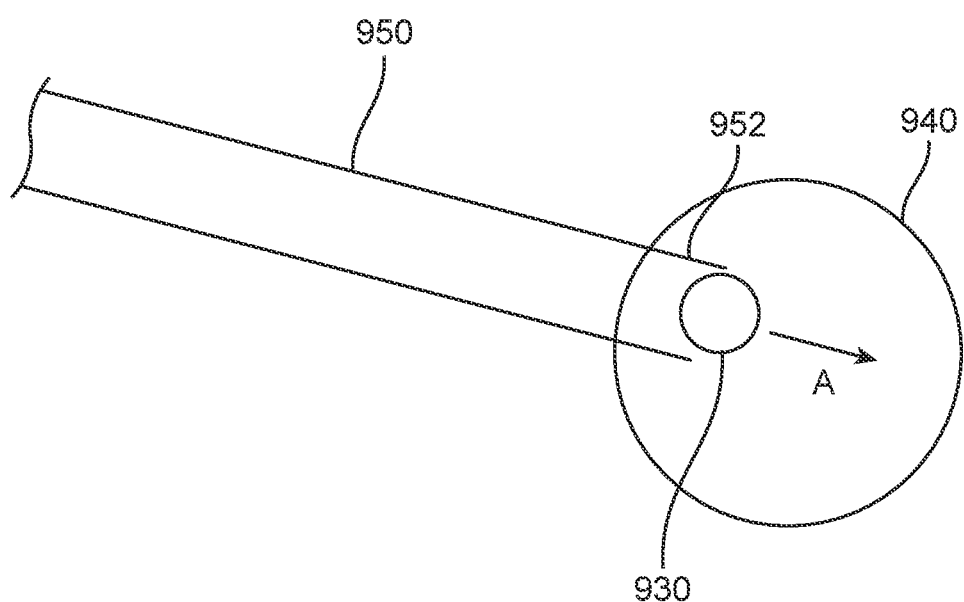

FIG. 9C illustrates how a particle 930 can be inserted into the body, for example within or at a tumor 940, using a delivery device 950 such as a syringe or a modified biopsy needle. As shown here, particle 930 exits a distal end 952 of the delivery device 950, in the direction indicated by arrow A, and enters the tumor 940. Any of a variety of methods can be used to insert microscopic (or mesoscopic) conducting particles into the tumor in a minimally invasive way, and this can be done even when the tumor may be behind bone.

Figure 9D:
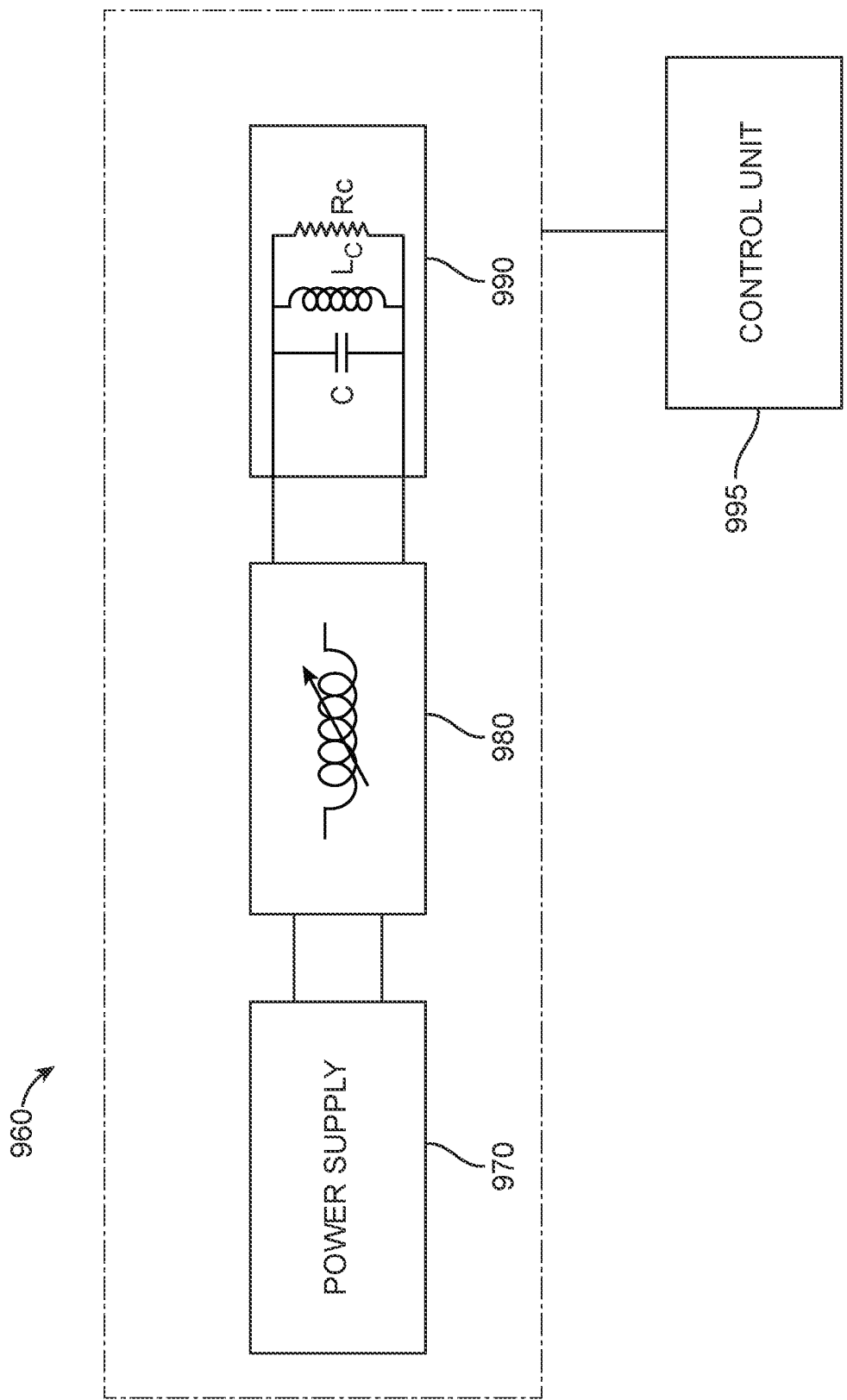

FIG. 9D depicts aspects of a magnetic field generation device 960, according to embodiments of the present invention. As shown here, a magnetic field generation device 970 can include a power supply 970, an impedance matching circuit 980, and a tank circuit 990. Power supply 970 can include any of a variety of power supply types, including without limitation line-frequency supplies, frequency multipliers, motor-generators, spark-gap converters, and solid-state inverters. Operation of the impedance matching circuit 980 can allow the power, voltage, and current values to reach their maximum values at the same time. Impedance matching circuits can include transformers, variable conductors, capacitors, and other electrical elements. This facilitates the delivery of maximum power from the power supply to the workpiece (e.g. particle). The tank circuit 990 has a coil, which typically includes a conductive material (e.g. copper) through which alternating current is passed, thereby creating a variable or oscillating magnetic field, which operates on the particle(s). In FIG. 9D, C represents capacitance, $R_C$ represents coil resistance, and $L_C$ represents coil inductance.

In some cases, a magnetic field generation device (e.g. which can include an electromagnet and an electronic oscillator) can further include or be in operative association with a control unit. As an example, the magnetic field generation device 960 shown in FIG. 9D can be in operative association with a control unit 995. In some embodiments the control unit may include or be in operative association with a user interface. The control unit can include or be in operative association with one or more processors (e.g. such as processor(s) 1004 depicted in FIG. 10) configured with instructions for performing one or more method steps and operations as described elsewhere herein. Similarly, the control unit may include or be in connectivity with any other component of a computer system (e.g. such as computer system 1000 depicted in FIG. 10).

Figure 10:
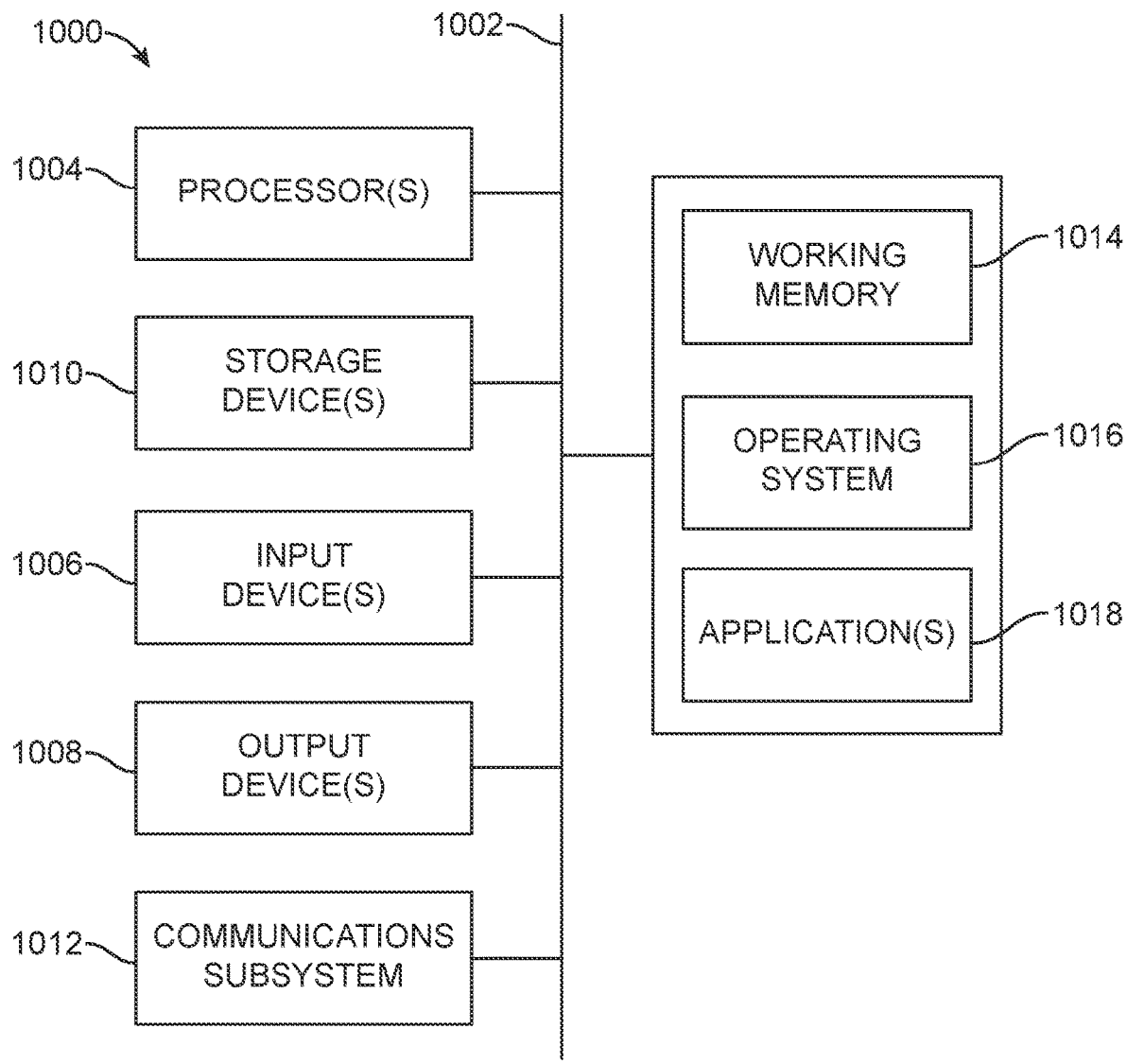
FIG. 10 depicts aspects of exemplary magnetic hyperthermia treatment systems and methods, according to embodiments of the present invention.

FIG. 10 depicts aspects of an exemplary computer system or device 1000 configured for use with any of the treatment devices or methods disclosed herein, according to embodiments of the present invention. An example of a computer system or device 1000 may include an enterprise server, blade server, desktop computer, laptop computer, tablet computer, personal data assistant, smartphone, any combination thereof, and/or any other type of machine configured for performing calculations. Any computing devices encompassed by embodiments of the present invention may be wholly or at least partially configured to exhibit features similar to the computer system 1000.

The computer system 1000 of FIG. 10 is shown comprising hardware elements that may be electrically coupled via a bus 1002 (or may otherwise be in communication, as appropriate). The hardware elements may include a processing unit with one or more processors 1004, including without limitation one or more general-purpose processors and/or one or more special-purpose processors (such as digital signal processing chips, graphics acceleration processors, and/or the like); one or more input devices 1006, which may include without limitation a remote control, a mouse, a keyboard, a keypad, a touchscreen, and/or the like; and one or more output devices 1008, which may include without limitation a presentation device (e.g., controller screen, display screen), a printer, and/or the like.

The computer system 1000 may further include (and/or be in communication with) one or more non-transitory storage devices 1010, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer system 1000 can also include a communications subsystem 1012, which may include without limitation a modem, a network card (wireless and/or wired), an infrared communication device, a wireless communication device and/or a chipset such as a Bluetooth device, 802.11 device, WiFi device, WiMax device, cellular communication facilities such as GSM (Global System for Mobile Communications), W-CDMA (Wideband Code Division Multiple Access), LTE (Long Term Evolution), and the like. The communications subsystem 1012 may permit data to be exchanged with a network (such as the network described below, to name one example), other computer systems, controllers, and/or any other devices described herein. In many embodiments, the computer system 1000 can further comprise a working memory 1014, which may include a random access memory and/or a read-only memory device, as described above.

The computer system 1000 also can comprise software elements, shown as being currently located within the working memory 1014, including an operating system 1016, device drivers, executable libraries, and/or other code, such as one or more application programs 1018, which may comprise computer programs provided by various embodiments, and/or may be designed to implement methods, and/or configure systems, provided by other embodiments, as described herein. By way of example, one or more procedures described with respect to the method(s) discussed herein, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code can be stored on a non-transitory computer-readable storage medium, such as the storage device(s) 1010 described above. In some cases, the storage medium might be incorporated within a computer system, such as computer system 1000. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, and the like), then takes the form of executable code.

It is apparent that substantial variations may be made in accordance with specific requirements. For example, customized hardware might also be used, and/or particular elements might be implemented in hardware, software (including portable software, such as applets, and the like), or both. Further, connection to other computing devices such as network input/output devices may be employed.

As mentioned elsewhere herein, in one aspect, some embodiments may employ a computer system (such as the computer system 1000) to perform methods in accordance with various embodiments of the disclosure. According to a set of embodiments, some or all of the procedures of such methods are performed by the computer system 1000 in response to processor 1004 executing one or more sequences of one or more instructions (which might be incorporated into the operating system 1016 and/or other code, such as an application program 1018) contained in the working memory 1014. Such instructions may be read into the working memory 1014 from another computer-readable medium, such as one or more of the storage device(s) 1010. Merely by way of example, execution of the sequences of instructions contained in the working memory 1014 may cause the processor(s) 1004 to perform one or more procedures of the methods described herein.

The terms "machine-readable medium" and "computer-readable medium," as used herein, can refer to any non-transitory medium that participates in providing data that causes a machine to operate in a specific fashion. In an embodiment implemented using the computer system 1000, various computer-readable media might be involved in providing instructions/code to processor(s) 1004 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1010. Volatile media may include, without limitation, dynamic memory, such as the working memory 1014.

Exemplary forms of physical and/or tangible computer-readable media may include a floppy disk, a flexible disk, hard disk, magnetic tape, or any other magnetic medium, a compact disc, any other optical medium, ROM, RAM, and the like, any other memory chip or cartridge, or any other medium from which a computer may read instructions and/or code. Various forms of computer-readable media may be involved in carrying one or more sequences of one or more instructions to the processor(s) 1004 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1012 (and/or components thereof) generally can receive signals, and the bus 1002 then can carry the signals (and/or the data, instructions, and the like, carried by the signals) to the working memory 1014, from which the processor(s) 1004 retrieves and executes the instructions. The instructions received by the working memory 1014 may optionally be stored on a non-transitory storage device 1010 either before or after execution by the processor(s) 1004.

It should further be understood that the components of computer system 1000 can be distributed across a network. For example, some processing may be performed in one location using a first processor while other processing may be performed by another processor remote from the first processor. Other components of computer system 1000 may be similarly distributed. As such, computer system 1000 may be interpreted as a distributed computing system that performs processing in multiple locations. In some instances, computer system 1000 may be interpreted as a single computing device, such as a distinct laptop, desktop computer, or the like, depending on the context.

A processor may be a hardware processor such as a central processing unit (CPU), a graphic processing unit (GPU), or a general-purpose processing unit. A processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. All features of the described systems are applicable to the described methods mutatis mutandis, and vice versa. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

According to some embodiments, machine-readable code instructions for, and/or data generated or used by, treatment devices and/or computing devices (which may include smart phones or other mobile computing devices) can be stored on or executed by any of a variety of computing modalities, including without limitation personal computers, servers (e.g. hosted and/or privately owned servers), internet connections, cloud hosts, cloud based storage, and the like.

As described elsewhere herein, a treatment device can include or be in operative association with a control unit. In some embodiments the control unit may include or be in operative association with a user interface. The control unit can include or be in operative association with one or more processors configured with instructions for performing one or more method steps (e.g. delivering heat or thermal energy to a treatment location of a patient). A control unit may include or be in connectivity with any component of a computer system.

All publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a patient presenting with a cancerous tumor, the method comprising:
    placing a conducting particle within the tumor of the patient, wherein the conducting particle has a diameter with a value within a range from about 20 microns to about 1000 microns; and
    heating the conducting particle with an oscillating magnetic field,
    wherein the conducting particle is attached with a filament.

2. The method according to claim 1, wherein the value of the diameter is about 500 microns.

3. The method according to claim 1, wherein the step of placing the conducting particle within the tumor of the patient comprises delivering the conducting particle with a delivery device selected from the group consisting of a biopsy needle, a bone marrow syringe, and a standard syringe.

4. The method according to claim 1, wherein the filament comprises a low conductivity material.

5. The method according to claim 1, wherein the particle is attached with the filament via an epoxy coupling, a welded coupling, or a clamped coupling.

6. The method according to claim 1, wherein the oscillating magnetic field is produced by a magnetic field generation device that is in operative association with a control unit.

7. The method according to claim 1, wherein the conducting particle comprises a chemically inert material.

8. The method according to claim 1, wherein the conducting particle comprises a material selected from the group consisting of gold and titanium.

9. The method according to claim 1, wherein the conducting particle comprises a material selected from the group consisting of a ferromagnetic material and a ferrimagnetic material.

10. A system for treating a patient presenting with a cancerous tumor, the system comprising:
    a conducting particle configured to be placed within the tumor of the patient, wherein the conducting particle has a diameter with a value within a range from about 20 microns to about 5000 microns, and wherein the conducting particle is attached with a filament;
    a magnetic field generation device; and
    a computer system in operative association with the magnetic field generation device, the computer system comprising a processor, an electronic storage location operatively coupled with the processor, and processor executable code stored on the electronic storage location and embodied in a tangible non-transitory computer readable medium, the processor executable code comprising machine-readable instructions that, when executed by the processor, cause the magnetic field generation device to generate an oscillating magnetic field that heats the conducting particle.

11. The system according to claim 10, wherein a frequency of the oscillating magnetic field has a value within a range from about 10 kHz to about 10000 kHz.

12. The system according to claim 10, wherein a frequency of the oscillating magnetic field has a value of about 50 kHz.

13. The system according to claim 10, wherein a strength of the oscillating magnetic field has a value of about 0.1 Tesla.

14. A method of providing heat to a treatment location of a patient, the method comprising:
    placing a conducting particle at the treatment location of the patient, wherein the conducting particle has a dimension with a value within a range from about 20 microns to about 5000 microns; and
    heating the conducting particle with an oscillating magnetic field, whereby the heated conducting particle provides heat to the treatment location,
    wherein the conducting particle is attached with a filament, and the method further comprises withdrawing the conducting particle from the treatment location after the conducting particle provides heat to the treatment location, by pulling on the filament.

15. The method according to claim 14, wherein the conducting particle has a shape selected from the group consisting of a sphere, a rectangular volume, an ellipsoid, a rod, and a cylinder.

16. The method according to claim 14, wherein the dimension has a value of about 500 microns.

17. The method according to claim 14, wherein the treatment location of the patient is within a tumor.

18. The method according to claim 17, wherein the tumor is a cancer tumor.

\* \* \* \* \*